United States Patent [19]

Funahashi et al.

[11] Patent Number: 4,871,513
[45] Date of Patent: Oct. 3, 1989

[54] TEST MEDIUM AND METHOD FOR DETECTING PHOSPHORUS SEGREGATES IN METALLIC MATERIAL

[75] Inventors: Yoshiko Funahashi; Yoshikazu Kamino; Yasuharu Matsumura; Senichi Harimaya, all of Chiba, Japan

[73] Assignee: Kawasaki Steel Corporation, Kobe, Japan

[21] Appl. No.: 61,210

[22] Filed: Jun. 12, 1987

Related U.S. Application Data

[62] Division of Ser. No. 765,245, Aug. 13, 1985, Pat. No. 4,681,857.

[30] Foreign Application Priority Data

Aug. 15, 1984 [JP] Japan ................................ 59-170227
Aug. 22, 1984 [JP] Japan ................................ 59-174828

[51] Int. Cl.$^4$ .......................... G01N 1/48; G01N 33/20
[52] U.S. Cl. ......................................... 422/56; 436/5; 436/78
[58] Field of Search ....................... 422/56, 55, 57, 61; 436/2, 4, 5, 78

[56] References Cited

U.S. PATENT DOCUMENTS 3,758,351  9/1973  Striedieck et al. ............... 156/659.1

Primary Examiner—Barry S. Richman
Assistant Examiner—T. J. Wallen
Attorney, Agent, or Firm—Young & Thompson

[57] ABSTRACT

An aqueous solution containing 0.00005 to 0.2 mol/l of copper ion and 0.0001 to 1.0 mol/l of nitrate ion is effective to detect phosphorus segregates in a metallic material, particularly cast steel. Segregated phosphorus can be detected by etching a surface of steel to be tested, attaching test paper onto the steel surface, applying the aqueous solution to the paper, maintaining the paper in contact with the steel surface until stains appear, and removing the paper from the steel surface. A red print is obtained when the solution is pH 6 or higher. A blue print is obtained by following the above steps, and further treating the paper with a color reagent containing molybdate ion, and then with a reducing agent.

4 Claims, 6 Drawing Sheets

TEST MEDIUM AND METHOD FOR DETECTING PHOSPHORUS SEGREGATES IN METALLIC MATERIAL

This application is a division of application Ser. No. 765,245, filed 8/13/85 now U.S. Pat. No. 4,681,857.

BACKGROUND OF THE INVENTION

This invention relates to a test medium and method for detecting phosphorus segregates, and more particularly, to such a method capable of rapidly and easily detecting the distribution of phosphorus in metallic materials such as continuously cast steel slabs and large-sized steel ingots.

Heretofore, segregation in large-sized steel ingots has been judged by sulfur printing. This method is by attaching photographic paper impregnated with aqueous sulfuric acid to a polished cross section of a large-sized steel ingot, thereby detecting hydrogen sulfide given off from segregated sulfur as stains on the photographic paper. This method has been widely used on the production line. Recently, however, steels subjected to low sulfide treatment and Ca treatment, such as steels resistant to hydrogen embrittlement cracking, have been put into practical use, and much progress has been made in the art to manufacture high purity steel and to minimize sulfur segregation in continuous castings. Such advanced steels having extremely low sulfur contents are difficult to detect solidification segregates by the conventional sulfur printing. It is thus desirable to detect phosphorus rather than sulfur for examining segregation.

Aside from the sulfur printing described above, a macroanalyzer is known as a device for examining the segregation of alloying elements. The macroanalyzer can quantitatively evaluate a planar section of a large-sized steel ingot by applying an electron beam to the section and detecting the spectrum of X-rays generated as in EPMA. However, this method is not applicable to a commercial production process because it uses an expensive device, the surface to be examined must be finished by emery paper of the order of #1,000, the measurement of a sample takes more than one hour, the configuration of a sample is limited, it cannot be applied to a wide section sample, and so on.

One known method of detecting phosphorus is the phosphorus printing reported by M. Niessner in 1932. This method is by attaching filter paper which has been immersed in liquid II shown below in Table 1 to a surface of steel to be examined for 3–5 minutes, removing the paper from the steel surface, and thereafter dipping the filter paper into liquid I for 3–5 minutes, thereby producing a printed image.

TABLE 1

| Liiquid I | |
|---|---|
| Stannous chloride saturated solution | 5 ml |
| Concentrated hydrochloric acid | 50 ml |
| Water | 100 ml |
| Alum | minor amount |
| Liquid II | |
| Ammonium molybdate | 5 g |
| Water | 100 ml |
| Nitric acid (specific gravity 1.2) | 35 ml |

Since the specimen surface is maintained in contact with 1.8 N nitric acid, the matrix is severely attacked and phosphorus is dissolved out there. When the removed test paper is dipped in liquid I, it turns blue over the entire surface. This method is only useful to estimate the amount of phosphorus in the matrix, but difficult to detect phosphorus segregates in commercial grade steels (see FIGS. 12 and 24).

SUMMARY OF THE INVENTION

It is an object of the present invention to provide a novel improved test medium and method capable of rapidly detecting and recording segregates in metallic materials such as Ca-loaded steels and low-sulfide steels over a large surface area as easily as by the sulfur printing described above. In this method, the element to be detected in place of sulfur is phosphorus, which has the great likelihood to segregate upon solidifying, and phosphorus segregates are detected on test paper as stains.

It is therefore, another object of the present invention to provide a novel method for detecting phosphorus segregation which takes the place of the conventional phosphorus printing method, can produce a clear printed image with high sensitivity through an easy printing operation, and is suitable for use in the control of an in-place production process.

As will be understood from the following description, the present process is called blue process when segregates are detected as blue spots and called red process when segregates are detected as red spots.

The blue process is first described.

According to a first aspect of the present invention, there is provided a test medium for use in detecting phosphorus segregates in a metallic material, in the form of an aqueous solution containing 0.00005 to 0.2 mol/l of copper ion and 0.0001 to 1.0 mol/l of nitrate ion.

According to a second aspect of the present invention, there is provided a test medium for use in detecting phosphorus segregates in a metallic material, in the form of a sheet impregnated with an aqueous solution containing 0.00005 to 0.2 mol/l of copper ion and 0.0001 to 1.0 mol/l of nitrate ion.

According to a third aspect of the present invention, there is provided a test medium for use in detecting phosphorus segregates in a metallic material, in the form of a sheet having an effective amount of copper and nitrate incorporated therein in a dry state.

According to a fourth aspect of the present invention, there is provided a method for detecting phosphorus segregates in a metallic material, comprising (a) attaching a test sheet onto that surface of a metallic material to be tested, (b) maintaining the sheet in contact with the metallic material surface in the presence of an aqueous solution comprising 0.00005 to 0.2 mol/l of copper ion and 0.0001 to 1.0 mol/l of nitrate ion for a sufficient time, (c) removing the sheet from the metallic material surface, and (d) treating the sheet from step (c) with a developing or color producing agent including molybdate.

According to an fifth aspect, the method as defined above further comprises (e) treating the sheet from step (d) with a reducing agent.

According to a sixth aspect, the method as defined above further comprises etching the surface of the metallic surface to be tested prior to step (a).

Next, the red process is descibed.

According to another aspect of the present invention, there is provided a test medium for use in detecting phosphorus segregates in a metallic material, in the form of an aqueous solution containing 0.00005 to 0.2 mol/l of copper ion and 0.0001 to 1.0 mol/l of nitrate ion and having a pH of at least 6.

According to the present invention, there is also provided a test medium for use in detecting phosphorus segregates in a metallic material, in the form of a sheet impregnated with an aqueous solution containing 0.00005 to 2 mol/l of copper ion and 0.0001 to 1.0 mol/l of nitrate ion and having a pH of at least 6.

According to the present invention, there is also provided a test medium for use in detecting phosphorus segregates in a metallic material, in the form of a sheet having an effective amount of copper and nitrate incorporated therein in a dry state.

According to still another aspect of the present invention, there is provided a method for detecting phosphorus segregates in a metallic material, comprising (a) attaching a test sheet onto that surface of a metallic material to be tested, (b) maintaining the sheet in contact with the metallic material surface in the presence of an aqueous solution comprising 0.00005 to 0.2 mol/l of copper ion and 0.0001 to 1.0 mol/l of nitrate ion at pH of at least 6.0 for a sufficient time, and (c) removing the sheet from the metallic material surface.

According to a further aspect, the method as defined above further comprises etching the surface of the metallic surface to be tested prior to step (a).

The metallic materials to which the present invention is applicable are generally carbon steels and low-alloy steels.

BRIEF DESCRIPTION OF THE DRAWINGS

The invention will be more fully understood when taken in conjunction with the accompanying drawings, in which.

DETAILED DESCRIPTION OF THE INVENTION

Figure 1:
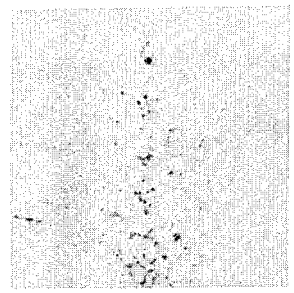
FIGS. 1 to 10 are photographic phosphorus prints representing phosphorus segregates in continuously cast steel billets in Examples 1 to 10.

The principle of the present invention will be briefly described. Like sulfur, phosphorus has the great likelihood of segregating upon solidification and is thus concentrated at the finally solidified region. Phosphorus rich portions are lower in electrochemical series and preferentially dissolved in etching solution. Ogura et al. reported in Journal of Japanese Metallurgy Associate, 45, 10, 1093 (1981), that the depth of grooves at grain boundary in steel etched with picric acid etchant is in quantitative relationship to the quantity of phosphorus segregated at grain boundary.

The inventors have found that by virtue of the preferential etching of phosphorus concentrated portions, phosphorus segregated on a solidified steel slab can be readily detected as blue spots in a short time by introducing an aqueous solution containing 0.00005 to 0.2 mol/l of copper ion and 0.0001 to 1.0 mol/l of nitrate ion, between that surface of the steel to be tested and a test sheet on which a pattern of phosphorus segregation is printable, followed by treating with a color producing agent and subsequently with a reducing agent. By introducing an aqueous solution containing 0.0005 to 0.2 mol/l of copper ion and 0.0001 to 1.0 mol/l of nitrate ion and having pH adjusted to at least 6.0 between that surface of the steel to be tested and a test sheet on which a pattern of phosphorus segregation is printable, red colored spots or stains representing segregated phosphorus appear on the surface of the test sheet. In this red process, post-treatments like color production and reduction are unnecessary.

The copper and nitrate ions used herein have the function to preferentially etch or attack electrochemically poorer local phosphorus segregates. Iron ions eluted from the segregated portion are adsorbed onto the test sheet where they precipitate as iron hydroxide, enabling detection of segregated phosphorus.

The sheets used in the practice of the invention may be any desired sheet-like articles of materials capable of bearing copper ion and nitrate ion such as wood and synthetic resins, and preferably paper, and most preferably baryta paper, but not limited thereto.

In any embodiment, it is necessary that an aqueous solution containing 0.00005 mol/l to 0.2 mol/l of copper ion and 0.0001 mol/l to 1.0 mol/l of nitrate ion contacts the surface of steel to be tested. Solutions containing less than 0.00005 mol/l of copper ion and 0.0001 mol/l of nitrate ion attack the steel too weakly to detect segregated phosphorus because stains or colored spots on a print is blurred whereas concentrations of higher than 0.2 mol/l of copper ion or 1.0 mol/l of nitrate ion result in deposits of the salt on the sheet and sticking of the sheet onto the specimen surface, rendering the sheet unuseful.

When applied by the red process the aqueous solution containing the specific amounts of copper and nitrate ions may preferably be adjusted to pH 6.0 or higher to facilitate the precipitation of iron ions eluted from the matrix as ferric hydroxide and ferric oxides onto the test sheet. By maintaining the test sheet in pressure contact with the specimen surface for several minutes, there is obtained a print clearly showing spots of segregated phosphorus as stains.

Examples of the cupric ion-supplying compounds include copper chloride $CuCl_2$, copper sulfate $CuSO_4$, copper bromide $CuBr_2$, copper carboxylate $Cu(COOH)_2$, and copper acetate $Cu(CH_3COO)_2$.

Examples of the nitrate ion suppling compounds include ammonium nitrate $NH_4NO_3$, sodium nitrate $NaNO_3$, potassium nitrate $KNO_3$, lithium nitrate $LiNO_3$, magnesium nitrate $Mg(NO_3)_2$ and calcium nitrate $Ca(NO_3)_2$.

The medium for detecting segregated phosphorus may vary in form. According to a first embodiment of the present invention, the detecting medium is in the form of an aqueous solution containing 0.00005 to 0.2 mol/l of copper ion and 0.0001 to 1.0 mol/l of nitrate ion. The solution may usually have a wider range of pH from about 0 to about 10, preferably lower pH, and especially pH of lower than 6 when it is used by the blue process. It should have a higher pH range from 6 to 14 when it is used by the red process. On use, a dry sheet or coupon is attached onto the surface of steel to be tested and the aqueous solution is applied to the sheet as by spraying, brushing or coating to cause the solution to reach the steel surface.

According to a second embodiment of the present invention, the detecting means is in the form of a wet sheet or coupon, that is, sheet or coupon impregnated or coated with the above-mentioned aqueous solution. The wet sheet, which has contained copper and nitrate ions in a proper amount, is ready for use, that is, it is simply attached or pressed to the surface of steel to be tested. In some cases, the test sheet may be coated with the solution immediately before it is pressed to the steel surface.

According to a third embodiment of the present invention, the detecting means is in the form of a dry sheet or coupon having copper and nitrate born thereon in a dry state. This dry sheet is prepared by impregnating a sheet with an aqueous solution containing copper and nitrate ions followed by drying. The dry sheet is used by attaching it to the surface of steel to be tested, and applying a suitable amount of water to the sheet such that an aqueous solution containing proper amounts of copper and nitrate ions and having an appropriate pH is present between the steel surface and the sheet.

The test sheets are attached to the surface of steel to be tested and maintained in contact with the steel surface for several minutes, for example, 3 to 10 minutes. The sheets are then removed from the steel surface. Iron ions eluted from the phosphorus segregated portion are adsorbed onto the test sheet and/or precipitated thereon as iron hydroxide if the solution has pH adjusted to 6 or higher, while similarly eluted phosphorus is also transferred to the sheet. The resulting sheets have an image of segregated phosphorus printed thereon.

The thus treated sheets may be immersed in a color developing or producing reagent, such as a reagent containing molybdate ion, and sensitive organic reagents such as macharite green. Examples of the molybdate ion-supplying compounds include ammonium molybdate, sodium molybdate, lithium molybdate, potassium molybdate, calcium molybdate, and magnesium molybdate.

The eluted phosphorus on the sheet may be developed with color reagents on the basis of molybdenum blue process. A typical example of the color reagent is an aqueous solution containing 0.1 to 10% by weight of molybdate ion and 0.5 to 5 N nitric acid. When the test sheet removed from the specimen surface is immersed in the color reagent, molybdenum yellow is formed at the site of eluted phosphorus, thereby enabling the detection of phosphorus segregates as yellow stains or spots.

When color reagents contain nitric acid of a normality outside the above-mentioned range or less than 0.1% by weight of ammonium molybdate, the amount of molybdenum yellow produced is insufficient to detect the segregation, whereas more than 10% by weight of molybdate ion makes difficult the identification of phosphorus segregates because of the coloring of molybdate ion itself.

The thus developed sheet may further be treated with a reagent containing reducing agents. Examples of the reducing agents include stannous chloride, hydroquinone, hydrazine sulfate, ascorbic acid, etc. A typical reducing reagent is an aqueous solution containing 0.1 to 20% by weight of stannous chloride and 0.5 to 6 N hydrochloric acid. Concentrations of less than 0.1% by weight of stannous chloride are not effective enough, while concentrations of more than 20% by weight produce no further reducing effect. Hydrochloric acid of less than 0.5 N causes the reduction of molybdate itself, and normalities of more than 6 N result in undesirable operating conditions due to vapor emission of concentrated hydrochloric acid. Other reducing agents may also be used in appropreate concentrations such that they have similar reducing effect as described above.

As understood from the above-mentioned principle of the present invention, the surface of steel to be tested for the presence of segregated phosphorus may preferably be etched prior to the above-described detecting process. The etching solutions used for the previous etching may be solutions containing at least one of mineral acids, organic acids and salts thereof, and an alcohol. Once the surface of steel to be tested is attacked by such an etching solution, the etching solution is removed and the steel surface is subjected to the above-described testing process.

Examples of the acids include mineral acids such as hydrochloric acid, sulfuric acid, perchloric acid, phosphoric acid, nitric acid, etc.; organic acids such as picric acid, salicylic acid, sulfosalicylic acid, acetic acid, formic acid, lactic acid, malic acid, etc.; and salts such as lithium chloride, copper chloride, calcium chloride, zinc chloride, iron chloride, aluminum chloride, copper sulfate, copper nitrate, tetramethyl ammonium chloride, etc. The alcohols which promote the attack on metal by acid may be any desired alcohols, for example, lower alkyl alcohols such as methanol, ethanol, and propanol as long as they are liquid at room temperature. The concentrations of acid and alcohol in the etching solution may vary with the characteristics of the steel surface to be tested including phosphorus concentration and the only requirement is that the alcohol is compatible with the acid in the solution.

Examples of the present invention are presented below by way of illustration and not by way of limitation.

The following examples are by the blue process.

EXAMPLE 1

A steel specimen was sectioned from a segregated region of a continuously cast slab of ordinary carbon steel having a phosphorus content of 0.02% by weight. It was polished with #240 emery paper and fully cleaned with absorbent wadding. A wet test paper coupon which was impregnated with an aqueous solution of 1% by weight of cupric chloride and 10% by weight of ammonium nitrate was attached to the surface of the specimen to be tested and maintained in pressure contact for 5 minutes. The test paper having an image of segregates developed was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 1.

EXAMPLE 2

Figure 2:
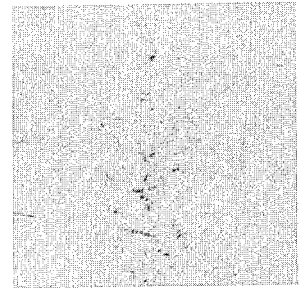

A steel specimen was taken out, polished, and cleaned in the same manner as in Example 1. A test paper coupon free of any agent was attached to the surface of the specimen to be tested. Absorbent wadding full of an aqueous solution containing 1% by weight of cupric sulfate and 10% by weight of lithium nitrate was forced to and moved throughout the paper to fully wet the paper. The paper was maintained in pressure contact with the specimen surface for 5 minutes. The test paper was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 2.

EXAMPLE 3

Figure 3:
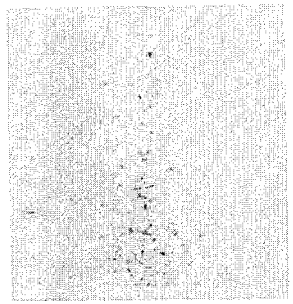

A steel specimen was taken out, polished, and cleaned in the same manner as in Example 1. A dry test paper coupon containing 6 grams of cupric nitrate per square meter was attached to the surface of the specimen to be tested. Absorbent wadding full of water was forced to and moved throughout the paper such that the test paper was fully wetted with the copper nitrate solution. The paper was maintained in pressure contact with the specimen surface for 5 minutes. The test paper was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 3.

EXAMPLE 4

Figure 4:
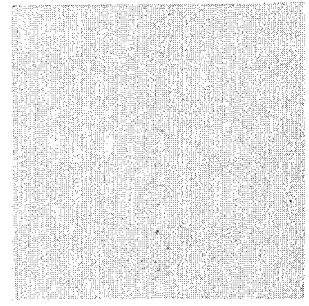

A steel specimen was taken out, polished, and cleaned in the same manner as in Example 1. A wet test paper coupon which was impregnated with an aqueous solution of 5% by weight of cupric nitrate was attached to the surface of the specimen to be tested and maintained in pressure contact for 5 minutes. The test paper was removed from the specimen surface, developed for 10 minutes with an aqueous solution of 2% by weight of ammonium molybdate and 1.75N nitric acid, and thoroughly washed with water. The resulting sheet was a print showing segregated phosphorus as yellow spots, as shown in FIG. 4.

EXAMPLE 5

Figure 5:
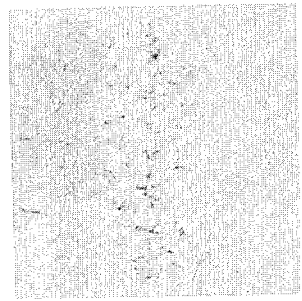

A steel specimen was taken out, polished, and cleaned in the same manner as in Example 1. A test paper coupon free of any agent was attached to the surface of the specimen to be tested. Absorbent wadding full of an aqueous solution containing 5% by weight of cupric nitrate was forced to and moved throughout the paper to fully wet the paper. The paper was maintained in pressure contact with the specimen surface for 5 minutes. The test paper was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 5.

EXAMPLE 6

Figure 6:
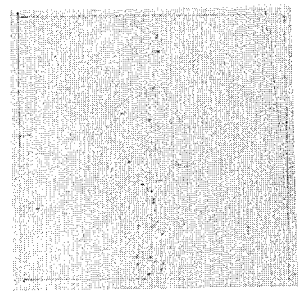

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a 5 vol% hydrochloric acid/ethanol solution for 5 minutes for etching. The etched specimen was fully cleaned with an alcohol and dried. A test sheet impregnated with an aqueous solution containing 7% by weight of cupric nitrate was attached to the surface of the specimen to be tested. The sheet was maintained in pressure contact with the specimen surface for 5 minutes. The test sheet was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 6.

EXAMPLE 7

Figure 7:
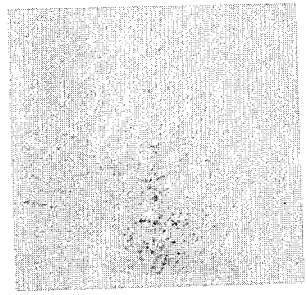

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a saturated picric acid/ethanol solution for 5 minutes for etching. The etched specimen was fully cleaned with ethanol and dried. A test sheet was attached to the specimen, wetted with an aqueous solution of 7% by weight cupric nitrate, and maintained in pressure contact with the specimen surface for 5 minutes. The test sheet was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 7.

EXAMPLE 8

Figure 8:
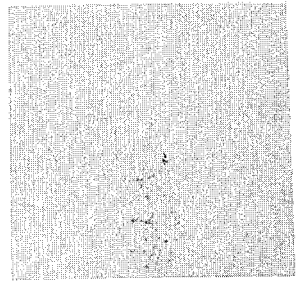

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a 5 wt % ferric chloride/ethanol solution for 5 minutes for etching. The etched specimen was fully cleaned with ethanol and dried. A dry test sheet containing 6 grams per square meter of cupric nitrate was attached to the specimen Absorbent wadding full of water was forced to and moved throughout the paper such that the test paper was fully wetted with the copper nitrate solution The sheet was maintained in pressure contact with the specimen surface for 5 minutes. The test sheet was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 8.

EXAMPLE 9

Figure 9:
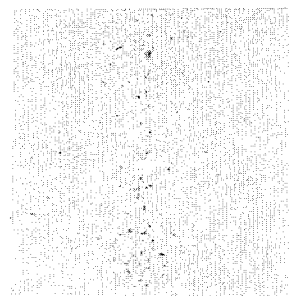

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a methanol solution of 4% by weight salicylic acid and 2% by weight lithium chloride for 5 minutes for etching. The etched specimen was fully cleaned with ethanol and dried. A test sheet wetted with an aqueous solution of 1% by weight of cupric nitrate and 10% by weight of ammonium nitrate was attached to the specimen and maintained in pressure contact with the specimen surface for 5 minutes. The test sheet was removed from the specimen surface, developed for 10 minutes with an aqueous solution of 2% by weight of ammonium molybdate and 1.75N nitric acid, reduced for 10 minutes with an aqueous solution of 7% by weight of stannous chloride and 4N hydrochloric acid, and thoroughly washed with water. There was obtained a printed image as shown in FIG. 9.

EXAMPLE 10

Figure 10:
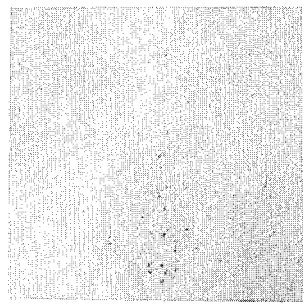

A freshly sectioned surface of a segregated region of a continuously cast slab of ordinary carbon steel having a phosphorus content of 0.02% by weight was polished with 180 emery paper and fully cleaned with absorbent wadding wetted with ethanol. The specimen was immersed in a 5 vol% hydrochloric acid/ethanol solution for 5 minutes for etching. The etched specimen was fully cleaned with alcohol and dried. A test sheet wetted with an aqueous solution containing 7% by weight of cupric nitrate was attached to the surface of specimen to be tested. The test sheet was maintained in pressure contact with the specimen surface for 5 minutes. The test sheet was removed from the specimen surface, developed for 10 minutes with an aqueous solution of 2% by weight of ammonium molybdate and 1.75N of nitric acid, and thoroughly washed with water. There was obtained a printed image as shown in FIG. 10.

Figure 11:
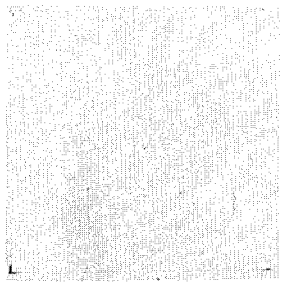
FIGS. 11, 12 and 13 are photographs taken on the same billet region by sulfur printing, conventional phosphorus printing, and a macroanalyzer, respectively.
Figure 12:
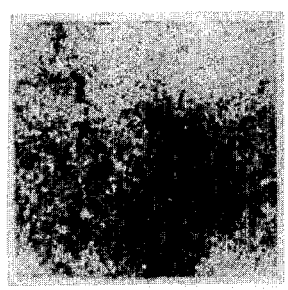
Figure 13:
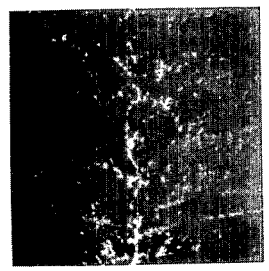

FIGS. 11, 12 and 13 are photographs taken on the same steel slab as used in Examples 1–10, by means of a sulfur printing, conventional phosphorus printing and a macroanalyzer, respectively. With respect to the phosphorus distribution pattern on a cross section of cast steel, the printed images shown in FIGS. 1–10 conform to the macroanalyzer photographs of FIGS. 13, proving that the present invention is fully effective in detecting phosphorus segregation. FIGS. 11 and 12 are difficult to detect phosphorus segregation. It should be noted that the prints of FIGS. 1–10 correspond of the macroanalyzer photograph of FIG. 13 but are mirror images thereof about a vertical center line. The present invention allows the microstructure to be observed as well as the central segregation.

The following examples are by the red process.

EXAMPLE 11

Figure 14:
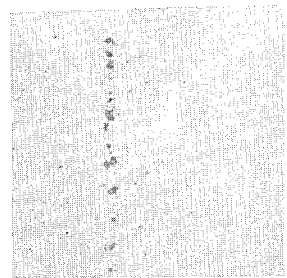
FIGS. 14 to 21 are photographic phosphorus prints showing phosphorus segregates in continuously cast billet used in Examples 11 to 14 and Exmaples 15 to 18.

A steel specimen was sectioned from a segregated region of a continuously cast slab of ordinary carbon steel having a phosphorus content of 0.02% by weight. It was polished with #240 emery paper and fully cleaned with dry absorbent wadding. A wet test paper coupon which was impregnated with an aqueous solution adjusted to pH 7.5 and containing by weight of cupric nitrate and 10% by weight of ammonium nitrate and 50% by volume of ethanol was attached to the surface of the specimen to be tested and maintained in pressure contact for 5 minutes The test paper was then removed from the specimen surface There was obtained a printed image as shown in FIG. 14.

EXAMPLE 12

Figure 15:
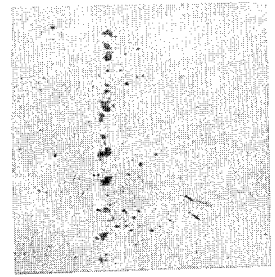

A steel specimen was taken out, polished, and cleaned in the same manner as in Example 11. A wet test paper coupon which was impregnated with an aqueous solution adjusted to pH 7.0 and containing 5% by weight of cupric nitrate was attached to the surface of the specimen to be tested and maintained in pressure contact for 5 minutes. The test paper was then removed from the specimen surface. There was obtained a printed image as shown in FIG. 15.

EXAMPLE 13

Figure 16:
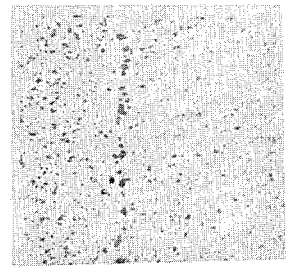

A steel specimen was taken out, polished, and cleaned in the same manner as in Example 11. A test paper coupon free of any agent was attached to the surface of the specimen to be tested. Absorbent wadding full of an aqueous solution adjusted to pH 7.5 and containing 1% by weight of cupric chloride and 10% by weight of lithium nitrate was forced to and moved throughout the paper to fully wet the paper. The paper was maintained in pressure contact with the specimen surface for 5 minutes The test paper was then removed from the specimen surface. There was obtained a printed image as shown in FIG. 16.

EXAMPLE 14

Figure 17:
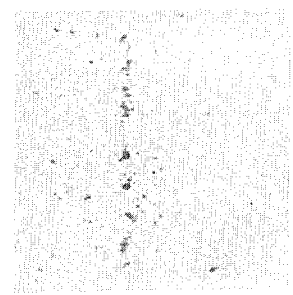

A steel specimen was taken out, polished, and cleaned in the same manner as in Example 11. A test paper coupon free of any agent was attached to the surface of the specimen to be tested. Absorbent wadding full of an aqueous solution adjusted to pH 8.0 and containing 5% by weight of cupric nitrate was forced to and moved throughout the paper to fully wet the paper The paper was maintained in pressure contact with the specimen surface for 5 minutes. The test paper was then removed from the specimen surface. There was obtained a printed image as shown in FIG. 17.

EXAMPLE 15

Figure 18:
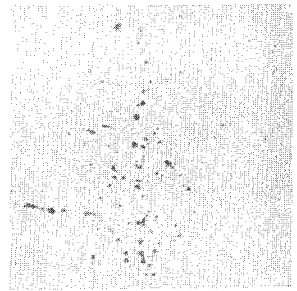

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a 5 vol % hydrochloric acid/ethanol solution for 5 minutes for etching. The etched specimen was fully cleaned with an alcohol and then a test sheet wetted with an aqueous solution adjusted to pH 7.5 containing 7% by weight of copper nitrate was attached to the specimen for 5 minutes. The test sheet was then removed from the specimen surface. There was obtained a printed image as shown in FIG. 18.

EXAMPLE 16

Figure 19:
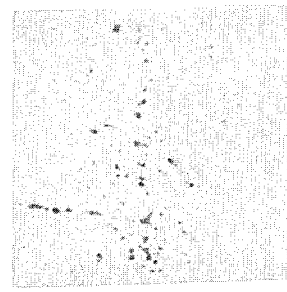

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a saturated picric acid/ethanol solution for 5 minutes for etching. The etched specimen was fully cleaned with ethanol. A test sheet was then attached to the specimen, wetted with an aqueous solution of 7% by weight cupric nitrate at pH 7.0, and maintained in contact with the specimen surface for 5 minutes. The test sheet was then removed from the specimen surface. There was obtained a printed image as shown in FIG. 19.

EXAMPLE 17

Figure 20:
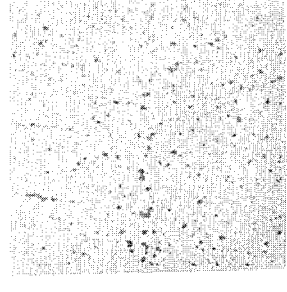

A freshly sectioned surface of a segregated region of a continuously cast slab of ordinary carbon steel having a phosphorus content of 0.02% by weight was polished with #180 emery paper and fully cleaned with absorbent wadding wetted with ethanol The specimen was immersed in an ethanol solution of 5% by weight ferric chloride for 5 minutes for etching. The etched specimen was fully cleaned with ethanol. A test sheet wetted with an aqueous solution adjusted to pH 8.0 and containing 1% by weight cupric chloride and 10% by weight of ammonium nitrate was attached to the specimen for 5 minutes The test sheet was then removed from the specimen surface There was obtained a printed image as shown in FIG. 20.

EXAMPLE 18

Figure 21:
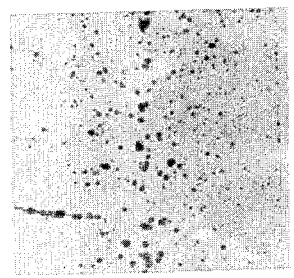

A freshly sectioned surface of a segregated region of a continuously cast slab of ordinary carbon steel having a phosphorus content of 0.02% by weight was polished with #180 emery paper and fully cleaned with absorbent wadding wetted with ethanol The specimen was immersed in a methanol solution of 4% by weight salicylic acid and 2% by weight of lithium chloride for 5 minutes for etching. The etched specimen was fully cleaned with ethanol A test sheet was attached to the specimen, wetted with an aqueous solution at pH 7.5 of 1% by weight cupric chloride and 10% by weight ammonium nitrate, and maintained in contact with the specimen surface for 5 minutes. The test sheet was then removed from the specimen surface There was obtained a printed image as shown in FIG. 21.

Figure 22:
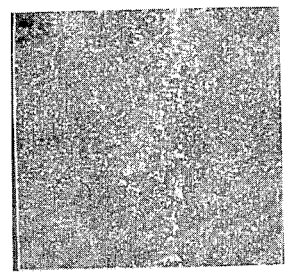
FIGS. 22 and 23 are macroanalyzer photographs showing segregated phosphorus patterns in the same regions as shown in FIGS. 14–17 and FIGS. 18–21, respectively.
Figure 23:
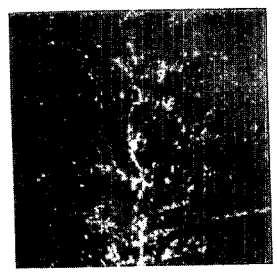
Figure 24:
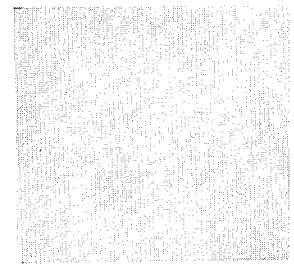
FIGS. 24 and 25 are photographs taken on the same billet region by sulfur printing and conventional phosphorus printing, respectivley.
Figure 25:
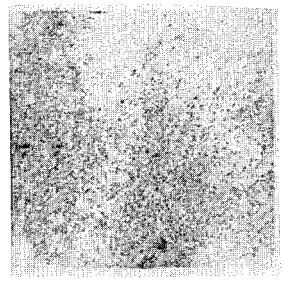

FIGS. 22 and 23 are macroanalyzer photographs showing segregated phosphorus patterns in regions corresponding to those shown in FIGS. 14–17 and FIGS. 18–21. FIGS. 24 and 25 are photographs taken by sulfur printing and conventional phosphorus printing, respectively. With respect to the phosophrus distribution pattern on a cross section of cast steel, the printed images shown in FIGS. 14–21 conform to the macroanalyzer photographs of FIGS. 22 and 23, proving that the present invention is fully effective in detecting phosphorus segregation. FIGS. 24 and 25 are difficult to detect phosphorus segregation. It should be noted that the prints of FIGS. 14–21 are the mirror images of the macroanalyzer photograph of FIGS. 22 and 23.

EFFECT OF THE INVENTION

As seen from the foregoing examples, the present invention allows segregated phosphorus to be detected without limitation on the size and shape of steel products to be tested. It has been found that this invention allows for detection of segregates in low sulfur steels and Ca-treated steels which could not be detected by the conventional sulfur printing Furthermore, unlike the sulfur printing, it eliminates troublesome operation in a dark room. Since no particular installation is needed for the detecting process because of the elimination of generation of any deleterious gases, the practice of the present invention is very easy during continuous steel casting in actual works. The present invention is thus very useful and benefitable in steel making It is also very convenient that prints showing segregated phosphorus can be stored as records.

What we claim is:

1. A test medium for use in detecting phosphorus segregates in a metallic material, comprising a wet sheet of paper impregnated with an aqueous solution containing 0.00005 to 0.2 mol/l of copper ion and 0.0001 to 1.0 mol/l of nitrate ion.

2. A test medium for use in detecting phosphorus segregates in a metallic material, comprising a sheet of paper having an effective amount of cooper ion supplying compound and nitrate ion supplying compound incorporated therein in a dry state, said amount being effective to preferentially etch a metallic material so as to detect phosphorus segregates when the sheet is saturated with water and applied to a surface of a metallic material.

3. A test medium for use in detecting phosphorus segregates in a metallic material, comprising a wet sheet of paper impregnated with an aqueous solution containing 0.00005 to 0.2 mol/l of copper ion and 0.0001 to 1.0 mol/l of nitrate ion and having a pH of at least 6.

4. A test medium for use in detecting phosphorus segregates in a metallic material, comprising a sheet of paper having an effective amount of copper ion supplying compound and nitrate ion supplying compound incorporated therein in a dry state such that there will be formed an aqueous solution containing 0.00005 to 0.2 mol/l of copper ion and 0.0001 to 1.0 mol/l of nitrate ion and having a pH of at least 6 when the sheet is saturated with water, said amount being effective to preferentially etch a metallic material so as to detect phosphorus segregates when the sheet saturated with water is applied to a surface of a metallic material.

* * * * *